(12) United States Patent
Muhs et al.

(10) Patent No.: US 8,585,951 B2
(45) Date of Patent: Nov. 19, 2013

(54) PROCESS FOR MAKING AN EMBOSSED WEB

(75) Inventors: Kevin Gerard Muhs, Hamilton, OH (US); Richard George Coe, Hamilton, OH (US); Keith Joseph Stone, Fairfield, OH (US); Sarah Beth Gross, Harrison, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 380 days.

(21) Appl. No.: 12/722,020

(22) Filed: Mar. 11, 2010

(65) Prior Publication Data

US 2010/0230857 A1    Sep. 16, 2010

Related U.S. Application Data

(60) Provisional application No. 61/159,906, filed on Mar. 13, 2009.

(51) Int. Cl.
*B29C 59/04*    (2006.01)

(52) U.S. Cl.
USPC ........... 264/293; 264/154; 264/156; 264/284; 264/285; 264/286; 264/509

(58) Field of Classification Search
USPC .......... 264/285, 286, 154, 156, 284, 293, 509
See application file for complete search history.

(56) References Cited

U.S. PATENT DOCUMENTS

| | | | |
|---|---|---|---|
| 3,484,835 A * | 12/1969 | Trounstine et al. | 264/284 |
| 3,719,736 A | 3/1973 | Woodruff | |
| 3,779,285 A | 12/1973 | Sinbaldo | |
| 3,911,187 A * | 10/1975 | Raley | 264/284 |
| 4,211,743 A | 7/1980 | Kos et al. | |
| 4,319,868 A | 3/1982 | Riemersma et al. | |
| 4,343,848 A | 8/1982 | Leonard, Jr. | |
| 4,546,029 A | 10/1985 | Cancio et al. | |
| 4,629,643 A * | 12/1986 | Curro et al. | 428/131 |
| 4,695,422 A * | 9/1987 | Curro et al. | 264/280 |
| 4,778,644 A | 10/1988 | Curro et al. | |
| 5,158,819 A | 10/1992 | Goodman et al. | |
| 5,281,371 A | 1/1994 | Tamura et al. | |

(Continued)

FOREIGN PATENT DOCUMENTS

| | | |
|---|---|---|
| DE | 34 39 555 A1 | 4/1986 |
| EP | 0 598 970 | 6/1994 |

(Continued)

OTHER PUBLICATIONS

International Search Report & Written Opinion, PCT/US2010/026920, mailed Aug. 7, 2010, 13 pages.

Nagarajan, Abbott, Yao; Rubber-Assisted Embossing Process; School of Polymer, Textile & Fiber Eng., Georgia Institute of Technology, Atlanta, GA 30332; ANTEC (2007) vol. 5, pp. 2921-2925, 5 pages.

Chang, Yang; Gas pressurized hot embossing for transcription of micro-features; Microsystem Technologies (2003) vol. 10, pp. 76-80, 5 pages; Springer-Verlag.

(Continued)

*Primary Examiner* — Timothy Kennedy
(74) *Attorney, Agent, or Firm* — Andrew J. Mueller; Jason J. Camp

(57) ABSTRACT

A process for making an embossed web. A precursor web is provided between a forming structure and a compliant substrate. The forming structure has a plurality of discrete apertures or depressions. Pressure is provided between the compliant substrate and the forming structure to force the precursor web into the apertures or depressions of forming structure to form the embossed web. The resulting embossed web has a plurality of discrete extended elements.

21 Claims, 8 Drawing Sheets

(56) References Cited

U.S. PATENT DOCUMENTS

| | | | |
|---|---|---|---|
| 5,650,215 | A | 7/1997 | Mazurek et al. |
| 5,670,110 | A | 9/1997 | Dirk et al. |
| 5,783,014 | A * | 7/1998 | Biagioli et al. .............. 156/209 |
| 5,858,515 | A * | 1/1999 | Stokes et al. .................. 156/167 |
| 5,871,607 | A * | 2/1999 | Hamilton et al. ............. 156/221 |
| 5,931,823 | A * | 8/1999 | Stokes et al. .................. 604/358 |
| 5,945,196 | A | 8/1999 | Ricker et al. |
| H1927 | H | 12/2000 | Chen et al. |
| 6,599,612 | B1 * | 7/2003 | Gray ............................. 428/132 |
| 6,719,742 | B1 | 4/2004 | McCormack et al. |
| 6,780,372 | B2 * | 8/2004 | Gray ............................. 264/504 |
| 6,846,445 | B2 | 1/2005 | Kim et al. |
| 6,852,475 | B2 * | 2/2005 | Stone et al. .................... 430/320 |
| 7,037,569 | B2 | 5/2006 | Curro et al. |
| 7,402,723 | B2 | 7/2008 | Stone et al. |
| 7,642,207 | B2 | 1/2010 | Boehmer et al. |
| 7,736,688 | B2 * | 6/2010 | Oetjen et al. .................... 427/2.1 |
| 7,799,254 | B2 | 9/2010 | Harvey et al. |
| 2001/0014796 | A1 | 8/2001 | Mizutani et al. |
| 2003/0119404 | A1 * | 6/2003 | Belau et al. .................... 442/361 |
| 2003/0187170 | A1 | 10/2003 | Burmeister |
| 2003/0201582 | A1 | 10/2003 | Gray |
| 2003/0228445 | A1 | 12/2003 | Vaughn et al. |
| 2004/0046290 | A1 | 3/2004 | Kim et al. |
| 2004/0119208 | A1 * | 6/2004 | Gray et al. .................... 264/504 |
| 2004/0121120 | A1 * | 6/2004 | Gray et al. .................... 428/131 |
| 2004/0122395 | A1 | 6/2004 | Stone et al. |
| 2004/0131820 | A1 | 7/2004 | Turner et al. |
| 2004/0161586 | A1 | 8/2004 | Cree et al. |
| 2004/0209041 | A1 * | 10/2004 | Muth et al. .................... 428/131 |
| 2005/0191496 | A1 | 9/2005 | Gray et al. |
| 2005/0279470 | A1 | 12/2005 | Redd et al. |
| 2006/0087053 | A1 | 4/2006 | O'Donnell et al. |
| 2006/0286343 | A1 | 12/2006 | Curro et al. |
| 2007/0062658 | A1 | 3/2007 | Wiwi et al. |
| 2007/0144693 | A1 | 6/2007 | Ruthven et al. |
| 2007/0261224 | A1 | 11/2007 | McLeod |
| 2008/0044777 | A1 * | 2/2008 | Gary et al. .................... 430/325 |
| 2008/0200320 | A1 | 8/2008 | Buckner et al. |
| 2008/0206529 | A1 * | 8/2008 | Ueminami et al. ........... 428/196 |
| 2008/0264275 | A1 | 10/2008 | Wilhelm et al. |
| 2010/0230866 | A1 * | 9/2010 | Gray et al. .................... 264/504 |

FOREIGN PATENT DOCUMENTS

| | | |
|---|---|---|
| GB | 1344054 A | 1/1974 |
| WO | WO 97/13633 A1 | 4/1997 |
| WO | WO 01/08869 A1 | 2/2001 |
| WO | WO 2008-120959 A1 | 10/2008 |

OTHER PUBLICATIONS

Dreuth, Heiden; Thermoplastic structuring of thin polymer films; Sensors and Actuators (1999) vol. 78, pp. 198-204, 7 pages; Institute of Applied Physics, University of Giessen, Heinrich-Buff-Ring 16 D-35392 Giessen, Germany; Elsevier Science S.A.

Heckele, Schomburg; Review on micro molding of thermoplastic polymers; Institute of Physics Publishing; Journal of Micromechanics and Microengineering (2004) vol. 14, No. 3, pp. R1-R14, 14 pages; IOP Publishing Ltd.

Kimerling, Liu, Kim, Yao; Rapid hot embossing of polymer microfeatures; Microsystem Technologies (2006) vol. 12, No. 8, pp. 730-735, 6 pages; School of Polymer, Textile and Fiber Eng., Georgia Institute of Technology, Atlanta GA 30332.

Nagarajan, Yao, Ellis, Azadegan; Through-Thickness Embossing Process for Fabrication of Three-Dimensional Thermoplastic Parts; School of Polymer, Textile & Fiber Eng., Georgia Institute of Technology, Atlanta GA 30332 and Delphi Research Labs, Shelby Township, Michigan 48315; Polymer Engineering and Science (2007) vol. 47, No. 12, pp. 2075-2084, 10 pages.

Rowland, King; Polymer deformation and filling modes during microembossing; Woodruff School of Mechanical Engineering, Georgia Institute of Technology, Atlanta, GA 30329-0405; Institute of Physics Publishing; Journal of Micromechanics and Microengineering (2004) vol. 14, No. 12, pp. 1625-1632, 8 pages; IOP Publishing Ltd.

Truckenmuller, Giselbrecht; Microthermoforming of flexible, not-buried hollow microstructures for chip-based life sciences applications; IEE Proceedings-Nanobiotechnology (Aug. 2004) vol. 151, No. 4, pp. 163-166; 4 pages.

Yao, Nagarajan; Cold Forging Method for Polymer Microfabrication; Department of Mechanical Engineering, Oakland University, Rochester, MI 48309; Polymer Engineering and Science (Oct. 2004) vol. 44, No. 10, pp. 1998-2004, 7 pages.

Yao, Nagarajan, Li, Yi; A Two-Station Embossing Process for Rapid Fabrication of Surface Microstructures on Thermoplastic Polymers; School of Polymer, Textile & Fiber Eng., Georgia Institute of Technology, Atlanta, GA 30332 and Department of Industrial, Welding and Systems Engineering, The Ohio State University, Columbus, OH 43210; Polymer Engineering and Science (2007) vol. 47, No. 4, pp. 530-539, 10 pages; Wiley InterScience; Society of Plastics Engineers.

Yao, Kuduva-Raman-Thanumoorthy; An enlarged process window for hot embossing; School of Polymer, Textile & Fiber Eng., Georgia Institute of Technology, Atlanta, GA 30332; Journal of Micromechanics and Microengineering (2008) vol. 18, pp. 1-7; 7 pages; IOP Publishing Ltd.

* cited by examiner

PROCESS FOR MAKING AN EMBOSSED WEB

CROSS REFERENCE TO RELATED APPLICATION

This application claims the benefit of U.S. Provisional Application No. 61/159,906, filed Mar. 13, 2009.

FIELD OF THE INVENTION

The invention relates to a process for making an embossed web comprising a plurality of discrete extended elements.

BACKGROUND OF THE INVENTION

Web materials, such as thermoplastic films, have a variety of uses including component materials of absorbent articles (such as topsheets and backsheets), packaging (such as flow wrap, shrink wrap, and polybags), trash bags, food wrap, dental floss, wipes, electronic components, and the like. For many of these uses of web materials, it can be beneficial for the web material to have a textured surface which can provide the surface of the web material with a desirable feel, visual impression, and/or audible impression.

Polymeric webs exhibiting a soft and silky tactile impression can be made via a vacuum forming process or a hydroforming process. With a typical vacuum forming process, a precursor web is heated and placed over a forming structure. Then a vacuum of air forces the precursor web to conform to the texture of the forming structure. The resulting polymeric web has texture that can provide a soft and silky tactile impression, depending upon the texture of the forming structure. While a vacuum forming process can be suitable for making a soft and silky polymeric web, a vacuum forming process is typically limited with respect to the amount of pressure capable of being exerted onto a precursor web. As a result, it is usually required to heat a precursor film to significantly soften or melt the precursor film prior to placement on the forming structure in order to vacuum form the precursor film to the forming structure. A vacuum forming process is therefore an inefficient process due to the heating step and the limited pressures generated by the process.

With a typical hydroforming process, a precursor web is placed over a forming structure and high pressure and high temperature water jets force the precursor web to conform to the texture of the forming structure. The resulting polymeric web can have texture that can provide a soft and silky tactile impression, depending upon the texture of the forming structure. A hydroforming process, although capable of producing soft and silky polymeric webs, is typically a costly and inefficient process involving the use of high pressure and high temperature water jets and subsequent drying steps, including dewatering steps.

Embossing is a process that typically involves the act of mechanically working a substrate to cause the substrate to conform under pressure to the depths and contours of a pattern engraved or otherwise formed on an embossing roll. It is widely used in the production of consumer goods. Manufacturers use the embossing process to impart a texture or relief pattern into products made of textiles, paper, synthetic materials, plastic materials, metals, and wood.

Embossing processes have been used to provide texture to polymeric films. However, such embossing processes typically require extruding a molten resin onto a forming structure or heating a precursor web before placement onto a forming structure and then embossing to produce an embossed web. The embossed web is then cooled, typically by cooling the embossing rolls or plates used to emboss the heated precursor web or molten resin. The cooling step is often utilized to set the texture in the embossed web. However, these heating and cooling steps add undesirable cost and inefficiency, as well as complexity, to the process. In addition, such embossing processes typically involve relatively large dwell times, which can result in slow, inefficient processes.

It is also typically difficult to impart relatively small scale texture to precursor webs using conventional embossing processes. Furthermore, typical embossing processes tend to produce embossed webs having relatively uniform thickness throughout the web.

Despite the knowledge in the art, there remains a desire to develop a more efficient process for making embossed webs that have desirable feel, visual impression, and/or audible impression, especially embossed webs exhibiting thinning in desirable areas of the embossed web. In certain aspects, a desired process is efficient with respect to the energy and resources required by the process. In certain aspects, a desired process is capable of running at high speeds. In certain aspects, a desired process is capable of running at relatively low temperatures, such as ambient temperature.

SUMMARY OF THE INVENTION

In one embodiment, a process for forming an embossed web, the process includes feeding a precursor web between a compliant substrate and a forming structure comprising a plurality of discrete apertures, discrete depressions, or combinations thereof. The apertures or depressions have a depth that is at least substantially equal to a thickness of the precursor web. The process further includes, applying pressure between the compliant substrate and the forming structure sufficient to force the compliant substrate into contact with the precursor web and sufficient to force portions of the precursor web into void volumes defined by the apertures or depressions, thereby forming the embossed web. The embossed web includes a plurality of discrete extended elements having open proximal ends.

Additional features of the invention may become apparent to those skilled in the art from a review of the following detailed description, taken in conjunction with the drawings, the examples, and the appended claims.

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

DETAILED DESCRIPTION OF THE INVENTION

Disclosed herein is a process for forming an embossed web that overcomes one or more of the aforementioned shortcomings of the prior art. Specifically, embodiments of the process now make possible a more efficient web embossing process. For example, embodiments of the process can now make possible the ability to impart relatively small scale texture to webs. Furthermore, embodiments of the process can now make possible the ability to avoid the cumbersome heating and cooling steps that the prior art required. Still further, embodiments of the process do not require the large dwell times required of prior art processes. In certain embodiments, the process can be used to form macro-scale structures for use, for example, as packaging materials such as bubble wrap.

Figure 1:
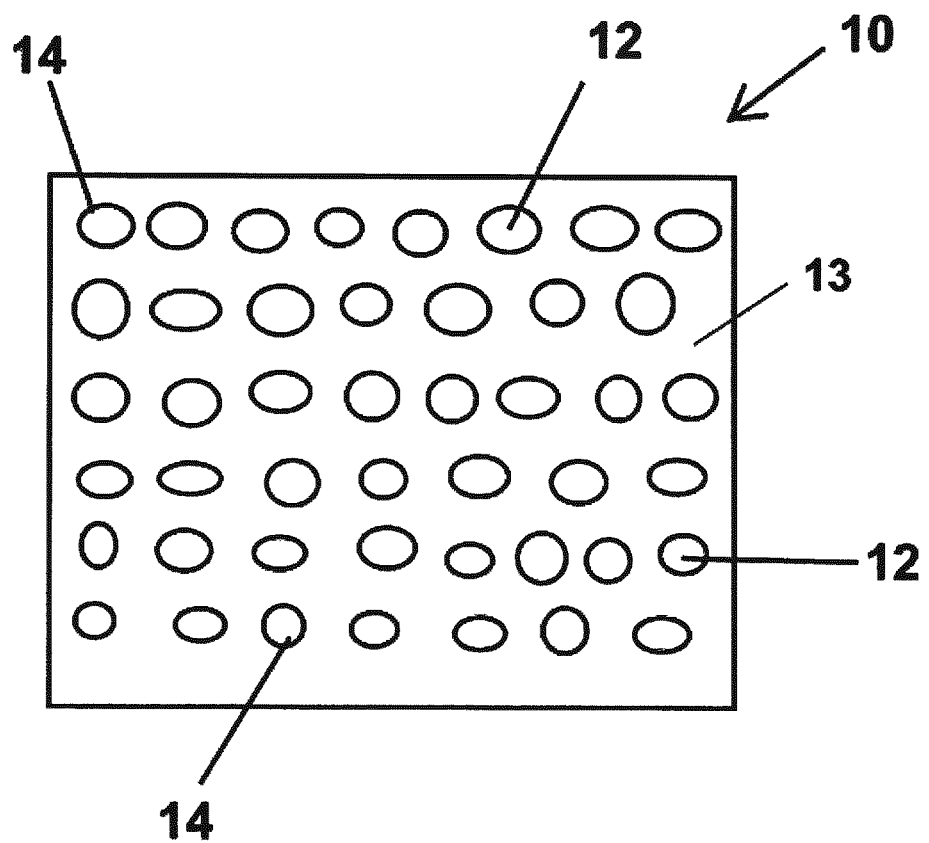
FIG. 1 is a top view of a forming structure in accordance with an embodiment of the disclosure.

With reference to FIG. 1, the process generally includes feeding a precursor web 34 between a compliant substrate 36 and a forming structure 10 comprising a plurality of discrete apertures 12, discrete depressions 14, or combinations thereof. The apertures 12 or depressions 14 have a depth that is at least substantially equal to a thickness of the precursor web 34, and preferably at least three times the thickness of the precursor web 34. The process further includes, applying pressure between the compliant substrate 36 and the forming structure 10 sufficient to force the compliant substrate 36 into contact with the precursor web 34 and sufficient to force portions of the precursor web 34 into void volumes defined by the apertures 12 or depressions 14, thereby forming the embossed web 16. The embossed web 16 includes a plurality of discrete extended elements 22 having open proximal ends 30. These aspects of the process are described in further detail below.

Forming Structure

Figure 2:
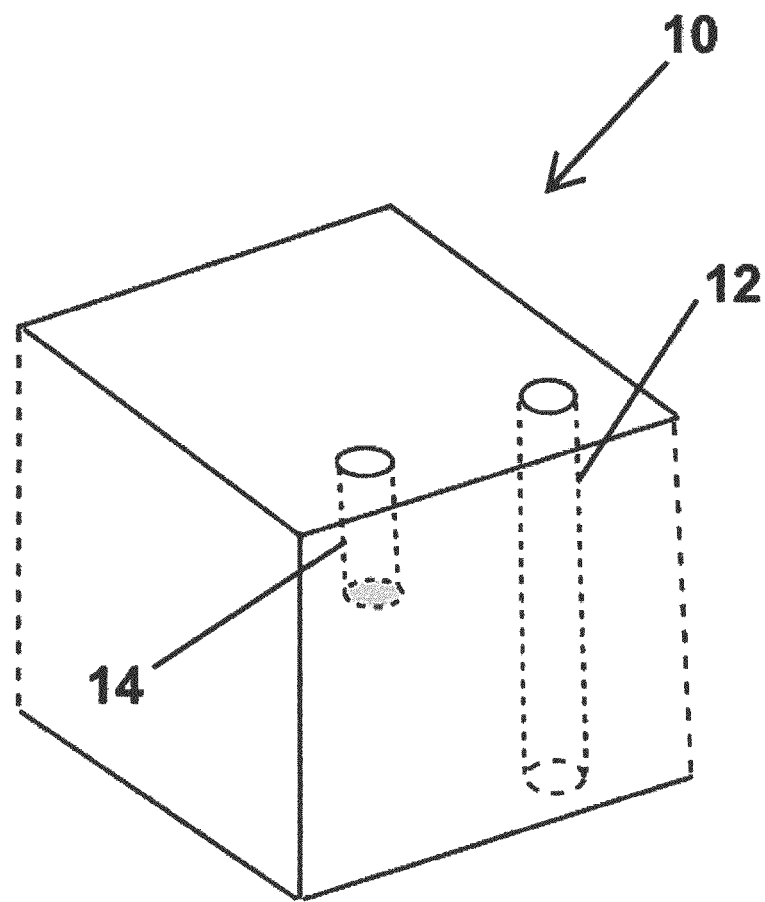
FIG. 2 is a perspective view of a forming structure in accordance with an embodiment of the disclosure illustrating the distinction between apertures and depressions.

Referring to FIGS. 1 and 2, a forming structure 10 useful in the process of the present disclosure includes a plurality of discrete apertures 12, discrete depressions 14, or a combination thereof. The forming structure 10 can further include lands 13 completely surrounding the discrete apertures 12 or depressions 14. The discrete apertures 12 or depressions 14 of the forming structure 10 are small in scale relative to typical patterns used on forming structures in conventional embossing processes. The process of the disclosure can produce embossed webs that include relatively high aspect ratio extended elements with thinned distal ends 24, even without heating the precursor web 34 and even at high speeds.

The forming structure 10 is sometimes referred to as a forming screen. FIG. 2 illustrates the distinction between apertures 12 and depressions 14. As used herein, "apertures" refers to an opening in the forming structure 10 that does not include a bottom surface limiting the depth of the opening. In contrast, as used herein, "depressions" refers to an opening in the forming structure 10 having a bottom surface limiting the depth of the opening to be less than the thickness of the forming structure 10. The bottom surface can be, for example, porous or non-porous. For example, the bottom surface can include an opening, having a width smaller than the diameter of the depression 14, that vents the depression 14 by allowing air to pass through the depression 14. In one embodiment, the forming structure has a means to allow any air trapped under the web to escape. For example, a vacuum assist can be provided to remove the air under the web so as not to increase the required compliant pressure. The bottom surface can be flat, rounded, or sharp. The forming structure 10 can be a solid roll, or have a thickness of about 25 microns to about 5000 microns, or about 100 microns to about 3000 microns. The depressions 14 can have a depth in a range of about 10 microns to about 500 microns, or about 25 microns to about 5000 microns. As used herein, the depth of the aperture corresponds to the thickness of the forming structure because the aperture 12 has no bottom surface limiting its depth. In one embodiment the apertures 12 and depressions 14 can have a depth substantially equal to the thickness of the precursor web 34, at least twice the thickness of the precursor web 34, or at least three times the thickness the precursor web 34.

The perimeter of the apertures 12 or depressions 14 on the precursor web 34 contacting surface of the forming structure 10 can have a straight edge or can have a radius of curvature as measured from the precursor web 34 contacting surface of the forming structure 10 into the aperture 12 or depression 14. The radius of curvature can be about 0 microns to about 2000 microns, preferably about 0 microns to about 25 microns, and more preferably about 2 microns to about 25 microns. In one embodiment, an angled taper, commonly known as a chamfer, is used. In one embodiment a combination of straight edges and radii are used.

The apertures 12 or depressions 14 have a diameter, which for a generally cylindrical structure is the inside diameter. For non-uniform cross-sections, and/or non-cylindrical structures of apertures 12 or depressions 14, diameter is measured as the average cross-sectional dimension of apertures 12 or depressions 14 at the top surface of the forming structure. Each aperture 12 or depression 14 can have diameter of about 10 microns to about 5 mm. Other suitable diameters include, for example, of about 50 microns to about 500 microns, about 65 microns to about 300 microns, about 75 microns to about 200 microns, about 100 microns to about 25000 microns, about 500 microns to about 5000 microns, or about 800 microns to about 2500 microns. In certain embodiments, the apertures 12 or depressions 14 can have larger diameters for forming macro-scale discrete extended elements. For example, the apertures 12 or depressions 14 can have a diameter up to about 2.5 centimeters, up to about 2 centimeters, up to about 1.5 centimeters, up to about 1 cm, up to about 0.5 centimeters, or up to about 0.1 centimeters.

In one embodiment, the diameter of apertures 12 or depressions 14 is constant or decreases with increasing depth. In another embodiment, the diameter of the apertures 12 or depressions 14 increases with increasing depth. For example, the discrete apertures 12 or depressions 14 can have a first diameter at a first depth and a second diameter at a second depth deeper than the first depth. For example, the first diameter can be larger than the second diameter. For example, the second diameter can be larger than the first diameter.

The sidewalls of the discrete apertures 12 or depressions 14 can be completely vertical or can be tapered. In one embodiment, the discrete apertures 12 or depressions 14 have tapered sidewalls. This can allow the web to more easily separate from the forming structure 10 after embossing. In one embodiment, the sidewalls will typically have a degree of taper of about 0° to about −50° to about 50°, about −30° to about 30°, about 0° to about 50°, about 2° to about 30°, or about 5° to about 25°.

The discrete apertures 12 or depressions 14 of the forming structure 10 can have a variety of different cross-sectional shapes, such as generally columnar or non-columnar shapes, including circular, oval, hour-glass shaped, star shaped, polygonal, and the like, and combinations thereof. Polygonal cross-sectional shapes include, but are not limited to, rectangular, triangular, hexagonal, or trapezoidal. In one embodiment, the discrete depressions 14 can have a length substantially equal to the length of the forming structure 10 so as to form grooves about substantially the entire length of the forming structure 10. For example, when the forming structure 10 is in the form of a roll, the grooves can be formed about the entire circumference of the roll. The grooves can be substantially straight (e.g., consistently parallel to the edge of the roll) or can be wavy.

In general, the forming structure 10, for a given portion of thereof, will include at least about 95 discrete apertures 12 or depressions 14 per square centimeter, at least about 240 discrete apertures 12 or depressions 14 per square centimeter, about 350 to about 10,000 discrete apertures 12 or depressions 14 per square centimeter, about 500 to about 5,000 discrete apertures 12 or depressions 14 per square centimeter, or about 700 to about 3,000 discrete apertures 12 or depressions 14 per square centimeter. In certain embodiments, the apertures 12 or depressions 14 can have a diameter greater than about 1 cm. Such larger sized apertures 12 or depressions 14 can be useful in forming embossed webs having larger-sized discrete extended elements, such as for example, for packing material. In these embodiments, the forming structure 10, for a given portion thereof, can include about 1 to about 5 discrete apertures 12 or depressions 14 per 10 square centimeters.

The apertures 12 or depressions 14 can have an average edge-to-edge spacing between two adjacent apertures 12 or depressions 14 of about 30 microns to about 1000 microns, about 30 microns to about 640 microns, about 150 microns to about 500 microns, or about 180 microns to about 430 microns. In certain embodiments, a portion (or area) of the forming structure 10 can include area densities of discrete apertures 12 or depressions 14 as described in the preceding paragraph, while other portions (or areas) of the forming structure 10 may include no discrete apertures 12 or depressions 14. The areas of the forming structure 10 having no discrete apertures 12 or depressions 14 can be located in a different horizontal plane. In other embodiments, the discrete apertures 12 or depressions 14 of the forming structure 10 can be located in different horizontal planes of the forming structure 10. The regions having no discrete apertures 12 or depressions 14 and/or the regions having discrete apertures 12 or depressions 14 located in different horizontal planes of the forming structure 10 can be in the form of a specific pattern or design, such as a flower, bird, ribbon, wave, cartoon character, logo, and the like, so that the embossed web 16 will have a region that stands out visually from, and/or has a different hand feel and/or a different sound when touched relative to, the remainder of the web. For example, the embossed web 16 can include a non-embossed region that stands out visually from, and/or has a different hand feel from embossed regions. U.S. Pat. No. 5,158,819, the disclosure of which is incorporated herein by reference, provides suitable examples of forming structures for use in these embodiments.

In one embodiment, a ratio of the average depth of the apertures 12 or depressions 14 to the thickness of the precursor web 34 is at least about 1:1, at least about 2:1, at least about 3:1, at least about 4:1, at least about 5:1, or at least about 10:1. This ratio can be important to ensure the precursor web 34 is sufficiently stretched so that it becomes permanently deformed to create an embossed web 16, especially at desirable process conditions and speed.

Forming structure 10 can be made of any material or materials that can be formed to have apertures 12 or depressions 14 having the necessary dimensions to make an embossed web 16 and is dimensionally stable over process temperature and pressure ranges experienced by forming structure 10.

In one embodiment, the forming structure 10 having the required relatively small scale apertures 12 or depressions 14 can be made by local, selective removal of material, such as by chemical etching, mechanical etching, or by ablating by use of high-energy sources such as electrical-discharge machines (EDM) or lasers, or by electron beam (e-beam), or by electrochemical machining (ECM). In one embodiment, the forming structure may be constructed by a photo etched laminate process generally in accordance with the teachings of U.S. Pat. No. 4,342,314.

In one method of making a suitable forming structure 10, a base material susceptible to laser modification is laser "etched" to selectively remove material to form apertures 12 or depressions 14. By "susceptible to laser modification", it is meant that the material can be selectively removed by laser light in a controlled manner, recognizing that the wavelength of light used in the laser process, as well as the power level, may need to be matched to the material (or vice-versa) for optimum results. Laser etching can be achieved by known laser techniques, selecting wavelength, power, and time parameters as necessary to produce the desired protruded element dimensions. Currently known materials susceptible to laser modification include thermoplastics such as polypropylene, acetal resins such as DELRIN® from DuPont, Wilmington Del., USA, thermosets such as crosslinked polyesters, or epoxies, or even metals such as aluminum, copper, brass, nickel, stainless steel, or alloys thereof. Optionally, thermoplastic and thermoset materials can be filled with particulate or fiber fillers to increase compatibility with lasers of certain wavelengths of light and/or to improve modulus or toughness to make more durable apertures 12 or depressions 14. For example, certain polymers, such as PEEK, can be laser machined to higher resolution and at higher speeds by uniformly filling the polymer with sufficient amounts of hollow carbon nanotube fibers.

In one embodiment, a forming structure 10 can be laser machined in a continuous process. For example, a polymeric material such as DELRIN® can be provided in a cylindrical form as a base material having a central longitudinal axis, an outer surface, and an inner surface, the outer surface and inner surface defining a thickness of the base material. It can also be provided as a solid roll. A moveable laser source can be directed generally orthogonal to the outer surface. The moveable laser source can be moveable in a direction parallel to the central longitudinal axis of the base material. The cylindrical base material can be rotated about the central longitudinal axis while the laser source machines, or etches, the outer surface of the base material to remove selected portions of the base material in a pattern that defines a plurality of discrete apertures 12 or depressions 14.

The forming structure 10 can be in the form of a flat plate, a roll, a belt, an endless belt, a sleeve, or the like. In one preferred embodiment, the forming structure 10 is in the form of a roll. In another preferred embodiment, the forming structure 10 is in the form of an endless belt. Endless belts can be formed in accordance with the teachings of U.S. Pat. Nos. 7,655,176, 6,010,598, 5,334,289, and 4,529,480.

The forming structure 10 can optionally further include discrete protruded elements. The discrete protruded elements can be sized and shaped and be formed as is described in U.S. Provisional Patent Application No. 61/159,906. If the forming structure 10 further includes protruded elements, the precursor web 34 can be forced onto the protruded elements of the forming structure 10, such that discrete extended elements 22 can be formed in the precursor web 34 extending from the surface of the precursor web 34 opposite the surface from which the discrete extended elements 22 formed by the apertures 12 or depressions 14 of the forming structure 10 are formed. As a result, a two-sided embossed web 16 can be created, having different patterns or dimensions of extended elements on each side of the embossed web 16. Depending upon the pressure generated between the forming structure 10 and compliant substrate 36, as well as the geometric shapes of the apertures 12 or depressions 14 and optional pillars or ridges of the forming structure 10, the discrete extended elements 22 of the embossed web 16 can have closed or open distal ends 24.

Compliant Substrate

A compliant substrate 36 is utilized to provide a force against the forming structure 10. At a minimum, the outer surface of the compliant substrate 36 (i.e., the surface of the compliant substrate 36 oriented towards the forming structure 10) includes a compliant material 40. For example, the compliant substrate 36 can include a rigid material 38 covered by a compliant material 40. The rigid material 38 can be a metal (such as steel), a plastic, or any other material that is significantly harder than the compliant material 40. The thickness of the compliant material 40 covering the rigid material 38 will typically be no greater than about 26 mm, and preferably about 1 mm to about 26 mm, more preferably about 1 mm to about 7 mm. Alternatively, the entire compliant substrate 36 can be made of a compliant material 40.

The compliant substrate 36 or compliant material 40 can include elastomers, felts, liquid-filled bladders, gas-filled bladders, and combinations thereof. In one embodiment, the compliant substrate 36 is a porous elastomer. The compliant substrate 36, or the compliant material 40 utilized in the compliant substrate 36, preferably has resilient properties (such as compression recovery) such that the compliant material 40 rebounds fast enough to facilitate the process, especially a continuous process.

The compliant substrate 36, or the compliant material 40 utilized in the compliant substrate 36, preferably also has enough durability to emboss large quantities of precursor web 34 material. As a result, the compliant substrate 36 preferably has a suitable degree of abrasion resistance, wherein the compliant substrate 36 will tend to be abraded by the forming structure 10 during the process.

The compliant substrate 36 can be in the form of a flat plate, a roll, a belt, an endless belt, a sleeve, or the like. In one embodiment, the compliant substrate 36 is a metal roll covered with a compliant material 40, such as an elastomer. In another embodiment, the compliant substrate 36 and the forming structure 10 are both in the form of rolls. In another embodiment, the compliant substrate 36 is a roll that has a diameter greater than the diameter of the forming structure 10 roll. In another embodiment, the compliant substrate 36 is a roll that has a diameter less than the diameter of the forming structure 10 roll. In another embodiment, the compliant substrate 36 roll has a diameter that is the same as the diameter of the forming structure 10 roll.

The compliant substrate 36, or the compliant material 40 utilized in the compliant substrate 36, will typically have a hardness of about 30 to about 80 durometer, preferably about 30 to about 60 durometer, and more preferably about 40 to about 70 durometer, on the Shore A scale. Hardness on the Shore A scale is typically determined by using an ASTM D2240 durometer, such as the Model 306 Type A Classic Style Durometer available from PTC Instruments of Los Angeles, Calif. It should be recognized that the compliant substrate 36 can exhibit varying hardness, for example lower hardness near the outer surface and higher hardness towards the inner surface of the compliant substrate 36 (i.e. varying hardness in the z-direction of the compliant substrate 36) or varying hardness across the outer surface of the compliant substrate 36 (i.e. varying hardness in the x-y plane of the compliant substrate 36).

The compliant material 40 utilized in the compliant substrate 36 will typically have a tensile modulus of about 1 to about 20 MPa, preferably about 2 to about 18 MPa, and more preferably about 3 to about 10 MPa. The tensile modulus of the compliant material 40 can be determined at a strain rate of $0.1\ \text{sec}^{-1}$.

Non-limiting examples of suitable compliant materials include natural rubber, urethane rubber, polyurethane rubber, chlorosulfonated polyethylene rubber (available under the tradename HYPALON® from DuPont), chloroprene rubber, norbornene rubber, nitrile rubber, hydrogenated nitrile rubber, styrene rubber, styrene-butadiene rubber, butadiene rubber, silicone rubber, ethylene-propylene-diene ("EPDM") rubber, isobutylene-isoprene rubber, felt (such as pressed wool felt), and the like. Particularly useful compliant materials are isoprene, EPDM, neoprene, and HYPALON® having a Shore A hardness of from about 30 to about 50 durometer, from about 40 to about 70 durometer, or from about 60 to about 80 durometer.

The compliant material 40 can also be a material, such as an absorbent core, that can be fed between a rigid material 38 and the forming structure 10 along with a precursor web 34. Such a material can serve to generate pressure against the precursor web 34 and forming structure 10 so as to emboss the precursor web 34. Such a material can then be later incorporated, along with the embossed web 16, into a finished consumer product, such as a feminine hygiene product.

The compliant substrate 36 can optionally include recessed regions of a depth sufficient to prevent the embossing of the precursor web 34 in the particular region, or only minimally emboss the precursor web 34 in the particular region. The optional recessed regions of the compliant substrate 36 can be in the form of a specific pattern or design, such as a flower, bird, ribbon, wave, cartoon character, logo, and the like, so that the embossed web 16 will have an unembossed region that stands out visually from, and/or has a different hand feel than, and/or has a different sound when touched than the embossed regions of the embossed web 16.

Precursor Web

A precursor web 34 is converted into an embossed web 16 according to the process of the disclosure. Suitable precursor webs include materials that can be deformed by pressure generated between the forming structure 10 and the compliant substrate 36, such that the precursor web 34 is able to be conformed to the topography of the forming structure 10 to produce an embossed web 16.

The precursor web 34 typically includes synthetic material, metallic material, biological material (in particular, animal-derived materials), or combinations thereof. The precursor web 34 can optionally include cellulosic material. In one embodiment, the precursor web 34 is free of cellulosic material. Non-limiting examples of suitable precursor webs include films, such as polymeric or thermoplastic films, foils, such as metallic foils (e.g. aluminum, brass, copper, and the like), webs comprising sustainable polymers, foams, fibrous nonwoven webs comprising synthetic fibers (e.g. TYVEK®), collagen films, chitosan films, rayon, cellophane, and the like. Suitable precursor webs further include laminates or blends of these materials.

If the precursor is a fibrous web, the fibrous web typically will have a high density such that it behaves similar to a film material. One example of such a high density fibrous web is TYVEK®.

In one embodiment, the precursor web 34 is a polymeric film. Suitable polymeric films include thermoplastic films such as polyethylene, polypropylene, polystyrene, polyethylene terephthalate (PET), polymethylmethacrylate (PMMA), polyvinyl alcohol (PVA), nylon, polytetrafluoroethylene (PTFE) (e.g., TEFLON), or combinations thereof. Suitable polymeric films can include blends or mixtures of polymers.

In certain embodiments, the precursor web 34 can be a web comprising a sustainable polymer, such as polylactides, polyglycolides, polyhydroxyalkanoates, polysaccharides, polycaprolactones, and the like, or mixtures thereof.

The thickness of the precursor web 34 prior to embossing will typically range from about 5 to about 300 microns, about 5 microns to about 150 microns, about 5 microns to about 100 microns, or about 15 microns to about 50 microns. Other suitable thicknesses includes about 1, 2, 3, 4, 5, 6, 7, 8, 9, 10, 20, 30, 40, 50, 60, 70, 80, 90, 100, 150, 200, 250, or 300 microns.

Precursor webs, such as polymeric webs, will typically have a glass transition temperature of about −100° C. to about 120° C., or about −80° C. to about 100° C., or other suitable ranges. Precursor webs, such as polymeric webs, can have a melting point of about 100° C. to about 350° C. For example, a precursor web 34 formed of LDPE or a blend of LDPE and LLDPE has a melting pointing of about 110° C. to about 122° C. A precursor web 34 formed of polypropylene has a melting point of about 165° C. A precursor web 34 formed of polyester has a melting point of about 255° C. A precursor web 34 formed of Nylon 6 has a melting point of about 215° C. A precursor web 34 formed of PTFE has a melting point of about 327° C.

In one embodiment, the process is carried out at a temperature less than the melting point of the precursor web. For example, the process can be carried out at 10° C. less than the melting point of the precursor web. In another embodiment, the process is carried out at a temperature substantially equal to the melting point of the precursor web. In one embodiment, the process is carried out at a temperature greater than the glass transition temperature of the precursor web.

Optionally, the precursor web 34 may be plasticized to make it less brittle prior to embossing in the process.

In one embodiment, the precursor web 34 is strain hardening. The strain hardening properties of the precursor web 34 can be desirable to facilitate conformation of the precursor web 34 to the discrete protruded elements of the forming structure 10. This can be preferred for producing embossed webs wherein closed distal ends 24 of the extended elements of the embossed web 16 are desired.

Precursor web 34 can be any material, such as a polymeric film, having sufficient material properties to be formed into an embossed web 16 described herein by the embossing process of the disclosure. The precursor web 34 will typically have a yield point and the precursor web 34 is preferably stretched beyond its yield point to form an embossed web 16. That is, the precursor web 34 should have sufficient yield properties such that the precursor web 34 can be strained without rupture to an extent to produce the desired discrete extended elements 22 with closed distal ends 24 or, in the case of an embossed web comprising discrete extended elements 22 having open distal ends 24, rupture to form open distal ends 24. As disclosed below, process conditions such as temperature can be varied for a given polymer to permit it to stretch with or without rupture to form the embossed web 16 having the desired discrete extended elements 22. In general, therefore, it has been found that preferred starting materials to be used as the precursor web 34 for producing the embossed web 16 exhibit low yield and high-elongation characteristics. In addition, as discussed previously, the precursor webs preferably strain harden. Examples of films suitable for use as the precursor web 34 include films comprising low density polyethylene (LDPE), linear low-density polyethylene (LLDPE), and blends of linear low-density polyethylene and low density polyethylene (LLDPE/LDPE).

Precursor web 34 must also be sufficiently deformable and have sufficient ductility for use as a precursor web 34. The term "deformable" as used herein describes a material which, when stretched beyond its elastic limit, will substantially retain its newly formed conformation, as well as exhibit thinning at or near the distal ends 24 of the discrete extended elements 22 of the resulting embossed web 16.

One material found suitable for use as a precursor web 34 is DOWLEX 2045A polyethylene resin, available from The Dow Chemical Company, Midland, Mich., USA. A film of this material having a thickness of 20 microns can have a tensile yield of at least 12 MPa; an ultimate tensile of at least 53 MPa; an ultimate elongation of at least 635%; and a tensile modulus (2% Secant) of at least 210 MPa (each of the above measures determined according to ASTM D 882). Other suitable precursor webs include polyethylene film that is about 25 microns (1.0 mil) thick and has a basis weight of about 24 grams per square meter ("gsm") available from available from RKW US, Inc. (Rome, Ga.) and polyethylene/polypropylene film having a basis weight of about 14 gsm and a thickness of about 15 microns available from RKW US, Inc.

The precursor web 34 can be a laminate of two or more webs, and can be a co-extruded laminate. For example, precursor web 34 can include two layers, and precursor web 34 can include three layers, wherein the innermost layer is referred to as a core layer, and the two outermost layers are referred to as skin layers. In one embodiment, the precursor web 34 includes a three layer coextruded laminate having an overall thickness of about 25 microns (0.001 in.), with the core layer having a thickness of about 18 microns (0.0007 in.); and each skin layer having a thickness of about 3.5 microns (0.00015 in.).

In one embodiment, the layers can include polymers having different stress-strain and/or elastic properties.

The precursor web 34 can be made using conventional procedures for producing multilayer films on conventional coextruded film-making equipment. Where layers comprising blends are required, pellets of the above described components can be first dry blended and then melt mixed in the extruder feeding that layer. Alternatively, if insufficient mixing occurs in the extruder, the pellets can be first dry blended and then melt mixed in a pre-compounding extruder followed by repelletization prior to film extrusion. Suitable methods for making precursor web 34 are disclosed in U.S. Pat. Nos. 5,520,875 and 6,228,462.

In general, the ability to form high area density (or low average center-to-center spacing) discrete extended elements 22 on the embossed web 16 can be limited by the thickness of precursor web 34.

In certain embodiments, the precursor web 34 can optionally further include a surfactant. If utilized, preferred surfactants include those from non-ionic families such as: alcohol ethoxylates, alkylphenol ethoxylates, carboxylic acid esters, glycerol esters, polyoxyethylene esters of fatty acids, polyoxyethylene esters of aliphatic carboxylic acids related to abietic acid, anhydrosorbitol esters, ethoxylated anhydrosorbitol esters, ethoxylated natural fats, oils, and waxes, glycol esters of fatty acids, carboxylic amides, diethanolamine condensates, and polyalkyleneoxide block copolymers. Molecular weights of surfactants selected can range from about 200 grams per mole to about 10,000 grams per mole. Preferred surfactants have a molecular weight of about 300 to about 1,000 grams per mole.

If utilized, the surfactant level initially blended into precursor web 34 can be as much as 10 percent by weight of the total precursor web 34. Surfactants in the preferred molecular weight range (300-1,000 grams/mole) can be added at lower levels, generally at or below about 5 weight percent of the total precursor web 34.

In certain embodiments, the precursor web 34 can also include titanium dioxide in the polymer blend. Titanium dioxide can provide for greater opacity of the embossed web 16. Titanium dioxide can be added at up to about 10 percent by weight of the precursor web 34, such as low density polyethylene.

Other additives, such as particulate material, e.g., particulate skin treatments or protectants, or odor-absorbing actives, e.g., zeolites, can optionally be added in one or more layers of precursor web 34. In some embodiments, embossed webs comprising particulate matter, when used in skin-contacting applications, can permit actives to contact the skin in a very direct and efficient manner. Specifically, in some embodiments, formation of discrete extended elements 22 can expose particulate matter at or near the distal ends 24 thereof. Therefore, actives such as skin care agents can be localized at or near distal ends 24 of the discrete extended elements 22 to permit direct skin contact with such skin care agents when the embossed web 16 is used in skin contacting applications.

The average particle size of the particulate material, if utilized in the precursor web 34, will typically be about 0.2 to about 200 microns or about 5 microns to about 100 microns. The use of certain particulate materials, such as mica interference particles, can dramatically improve the visual appearance of the embossed web 16.

The precursor web 34 can also optionally include colorants, such as pigment, lake, toner, dye, ink or other agent used to impart a color to a material, to improve the visual appearance of the embossed web 16.

Suitable pigments herein include inorganic pigments, pearlescent pigments, interference pigments, and the like. Non-limiting examples of suitable pigments include talc, mica, magnesium carbonate, calcium carbonate, magnesium silicate, aluminum magnesium silicate, silica, titanium dioxide, zinc oxide, red iron oxide, yellow iron oxide, black iron oxide, carbon black, ultramarine, polyethylene powder, methacrylate powder, polystyrene powder, silk powder, crystalline cellulose, starch, titanated mica, iron oxide titanated mica, bismuth oxychloride, and the like.

Suitable colored webs are described in co-pending U.S. application Ser. No. 12/721,947, filed Mar. 11, 2010 entitled "COLORED WEB MATERIAL COMPRISING A PLURALITY OF DISCRETE EXTENDED ELEMENTS" (P&G Case 11634) and U.S. application Ser. No. 12/721,965, filed Mar. 11, 2010 entitled "WEB MATERIAL EXHIBITING VIEWING-ANGLE DEPENDENT COLOR AND COMPRISING A PLURALITY OF DISCRETE EXTENDED ELEMENTS".

The precursor web 34 can also optionally include fillers, plasticizers, and the like.

Embossed Web

Figure 3:
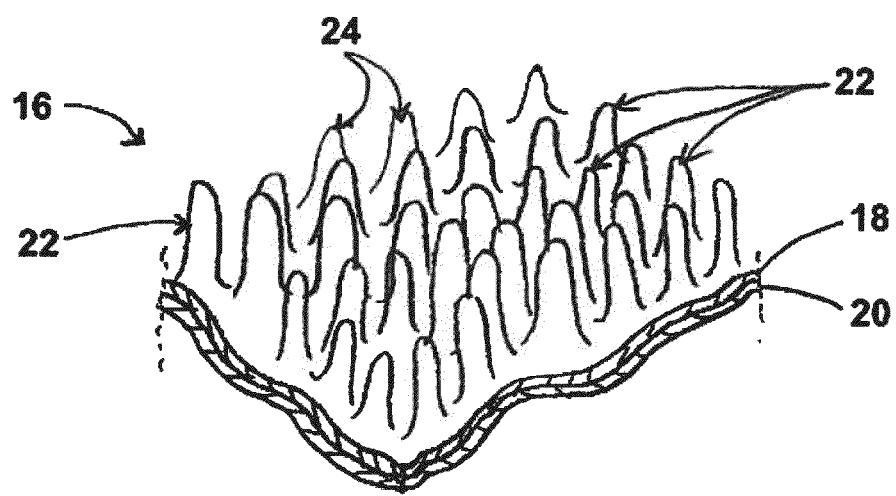
FIG. 3 is a perspective view of a portion of an embossed web formed by a process in accordance with an embodiment of the disclosure.
Figure 4:
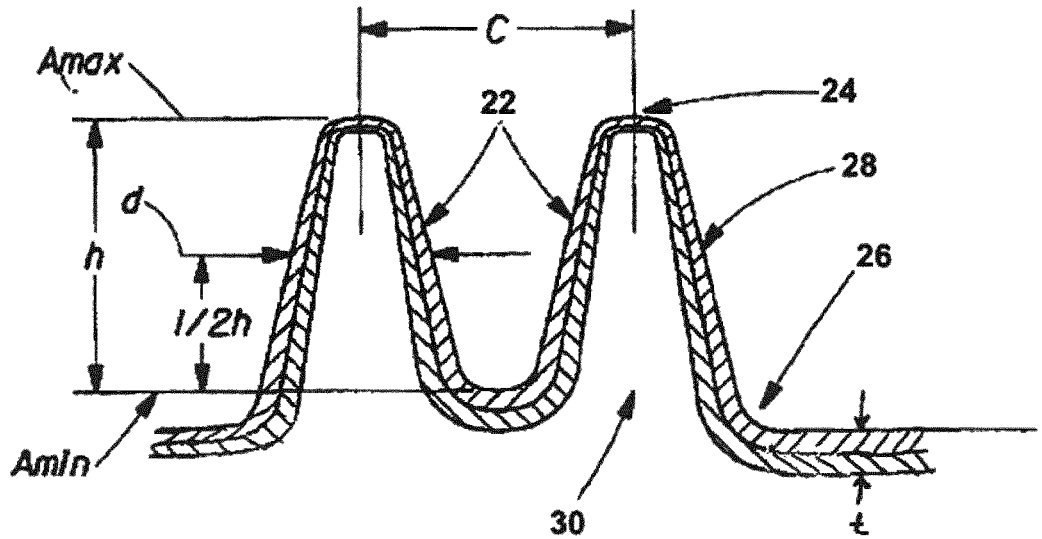
FIG. 4 is a cross-sectional view of a portion of an embossed web formed by a process in accordance with an embodiment of the disclosure.
Figure 5:
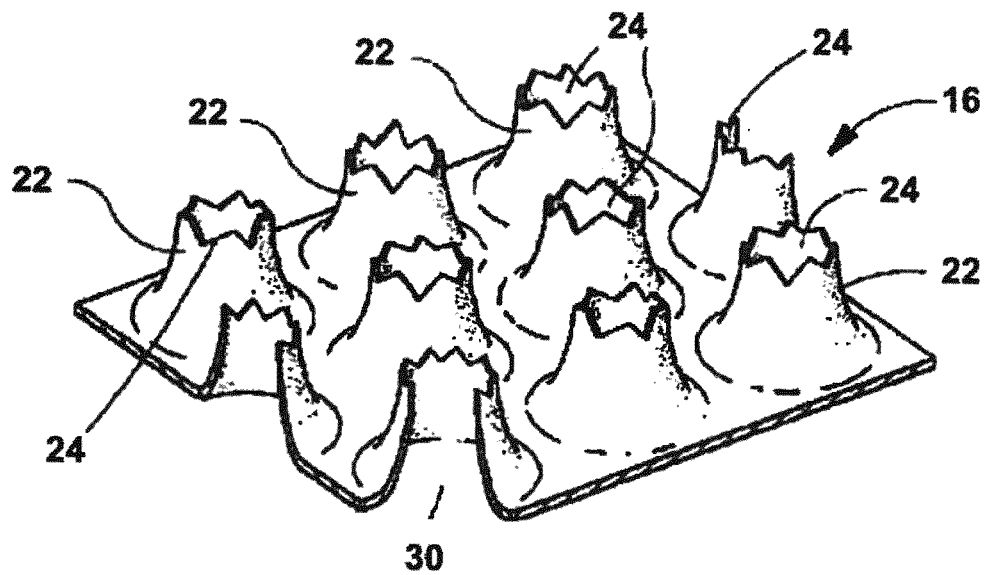
FIG. 5 is a perspective view of a portion of an embossed web having discrete extended elements with open distal ends formed by a process in accordance with an embodiment of the disclosure.
Figure 6:
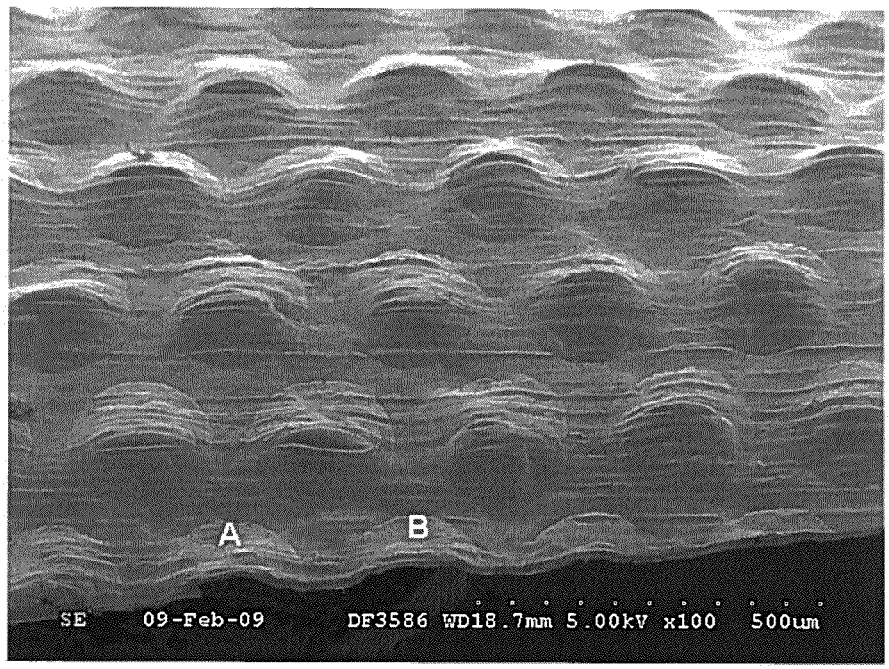
FIG. 6 is a photomicrograph of an embossed web having discrete extended elements with closed distal ends formed by a process in accordance with an embodiment of the disclosure.
Figure 7:
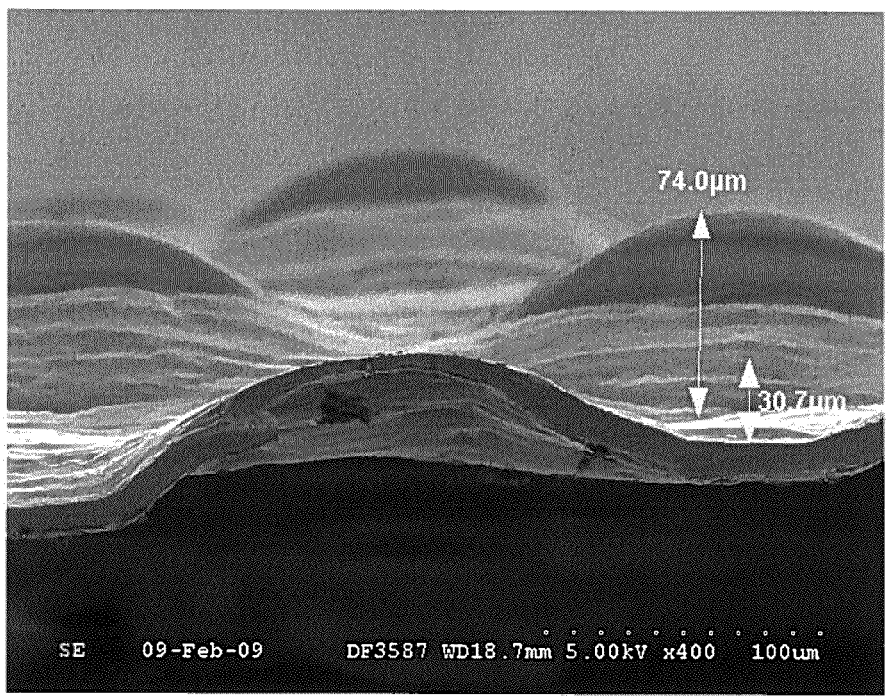
FIG. 7 is a magnified photomicrograph of the embossed web of FIG. 6.
Figure 8:
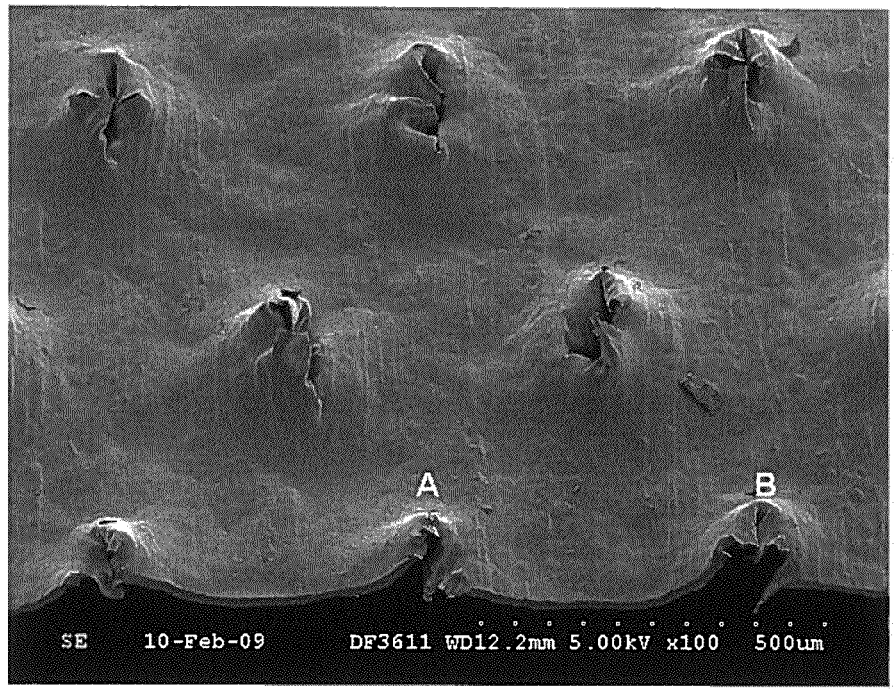
FIG. 8 is a photomicrograph of an embossed web having discrete extended elements with open distal ends formed by a process in accordance with an embodiment of the disclosure.
Figure 9:
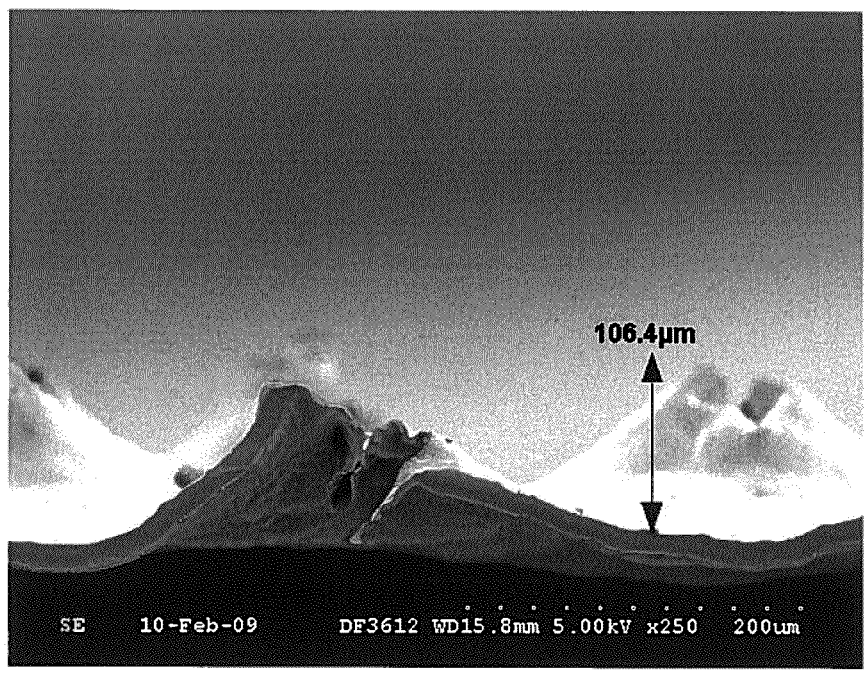
FIG. 9 is a magnified photomicrograph of the embossed web of FIG. 8.

The precursor web 34 is processed according to the process of the disclosure to form an embossed web 16 that can have various desired structural features and properties such as desired soft hand feel and an aesthetically pleasing visual appearance. The precursor web 34 is positioned between the forming structure 10 and the compliant substrate 36 provided to conform the precursor web 34 to the discrete apertures 12 or depressions 14 of the forming structure 10. Referring to FIG. 3, an embossed web 16 having discrete extended elements 22 is thereby produced. As shown in FIG. 4, the discrete extended elements 22 have open proximal ends 30 and open (as shown in FIGS. 5, 8 and 9) and or closed (as shown in FIGS. 3, 4, 6, and 7) distal ends 24.

In one embodiment, the embossed web 16 resulting from the process described herein can have a structure 10 similar to that described in detail in U.S. Pat. Nos. 7,402,723 or 7,521,588.

The three-dimensional embossed web 16 is produced from a precursor web 34, which can be a single layer of web material or a multilayer coextruded or laminate web material as described hereinbefore. Laminate film materials may be coextruded, as is known in the art for making laminate films, including films comprising skin layers. In the embodiment illustrate in FIG. 3, the precursor web 34 is a two layer laminate film comprising a first layer 18 and a second layer 20.

The discrete extended elements 22 are formed as protruded extensions of the web, generally on a first surface 26 thereof. The number, size, and distribution of discrete extended elements 22 on the embossed web 16 can be predetermined based on desired soft feel, sound effects and visual effects. For applications such as a topsheet, backsheet or release paper wrapper in disposable absorbent articles, or packaging, it can be desired that the discrete extended elements 22 protrude only from one surface of embossed web 16. Therefore, when the embossed web 16 is used as a topsheet in a disposable absorbent article, the embossed web 16 can be oriented such that the discrete extended elements 22 are skin contacting for superior softness impression. Moreover, having discrete extended elements 22 with closed distal ends 24 can result in reduced rewet, i.e., reduced amounts of fluid being re-introduced to the surface of the topsheet after having been first passed through apertures 12 of the topsheet to underlying absorbent layers.

Referring to FIG. 4, the discrete extended elements 22 can be described as protruding from a first surface 26 of the embossed web 16. As such, the discrete extended elements 22 can be described as being integral with precursor web 34, and formed by permanent local plastic deformation of the precursor web 34. The discrete extended elements 22 can be described as having a side wall(s) 28 defining an open proximal portion and a closed or open distal end 24. The discrete extended elements 22 each have a height h measured from a minimum amplitude $A_{min}$ between adjacent extended elements to a maximum amplitude $A_{max}$ at the closed or open distal end 24. The discrete extended elements 22 have a diameter d, which for a generally cylindrical structure 10 is the outside diameter at a lateral cross-section. By "lateral" is meant generally parallel to the plane of the first surface 26. For generally columnar discrete extended elements 22 having non-uniform lateral cross-sections, and/or non-cylindrical structures of discrete extended elements 22, diameter d is measured as the average lateral cross-sectional dimension at ½ the height h of the discrete extended element. Thus, for each discrete extended element, an aspect ratio, defined as h/d, can be determined The discrete extended element can have an aspect ratio h/d of at least about 0.2, at least about 0.3, at least about 0.5, at least about 0.75, at least about 1, at least about 1.5, at least about 2, at least about 2.5, or at least about 3. The discrete extended elements 22 will typically have a height h of at least about 30 microns, at least about 50 microns, at least about 65, at least about 80 microns, at least about 100 microns, at least about 120 microns, at least about 150 microns, or at least about 200 microns. The extended elements will typically be at least the same height as the thickness of the precursor web, or at least 2 times the thickness of the precursor web, or preferably at least 3 times the thickness of the precursor web. The discrete extended elements 22 will typically have a diameter d of about 50 microns to about 5,000 microns, about 50 microns to about 3,000 microns, about 50 microns to about 500 microns, about 65 microns to about 300 microns, or about 75 microns to about 200 microns. In certain embodiments, the discrete extended elements 22 can have a larger diameter d up to about 2.5 centimeters, up to about 2 centimeters, up to about 1.5 centimeters, up to about 1 cm, up to about 0.5 centimeters, or up to about 0.1 centimeters.

For discrete extended elements 22 that have generally non-columnar or irregular shapes, a diameter of the discrete extended element can be defined as two times the radius of gyration of the discrete extended element at ½ height.

For discrete extended elements that have shapes, such as ridges, that extend lengthwise across the entire web material such that the extended elements have a portion of the sidewalls of the extended elements that are open, a diameter of a discrete extended element can be defined as the average minimal width between two opposing sidewalls of the extended element at ½ height.

In general, because the actual height h of any individual discrete extended element can be difficult to determine, and because the actual height may vary, an average height $h_{avg}$ of a plurality of discrete extended elements 33 can be determined by determining an average minimum amplitude $A_{min}$ and an average maximum amplitude $A_{max}$ over a predetermined area of the embossed web 16. Such average height $hp_{avg}$ will typically fall within the ranges of heights described above. Likewise, for varying cross-sectional dimensions, an average diameter $d_{avg}$ can be determined for a plurality of discrete extended elements 33. Such average diameter $d_{avg}$ will typically fall within the ranges of diameters described above. Such amplitude and other dimensional measurements can be made by any method known in the art, such as by computer aided scanning microscopy and data processing. Therefore, an average aspect ratio $AR_{avg}$ of the discrete extended elements 22 for a predetermined portion of the embossed web 16 can be expressed as $h_{avg}/d_{avg}$.

In one embodiment, the diameter of a discrete extended element is constant or decreases with increasing amplitude (amplitude increases to a maximum at closed or open distal end 24). The diameter, or average lateral cross-sectional dimension, of the discrete extended elements 22 can be a maximum at proximal portion and the lateral cross-sectional dimension steadily decreases to distal end. This structure 10 is believed to be desirable to help ensure the embossed web 16 can be readily removed from the forming structure 10. In another embodiment, the diameter of the discrete extended elements 22 increases with increasing amplitude. For example, the discrete extended elements 22 can have a mushroom shape.

Thinning of the precursor web 34 can occur due to the relatively deep drawing required to form high aspect ratio discrete extended elements 22. For example, thinning can be observed at or near the closed or open distal ends 24. By "observed" is meant that the thinning is distinct when viewed in magnified cross-section. Such thinning can be beneficial as the thinned portions offer little resistance to compression or shear when touched. For example, when a person touches the embossed web 16 on the side exhibiting discrete extended elements 22, the fingertips of the person first contact the closed or open distal ends 24 of the discrete extended elements 22. Due to the high aspect ratio of the discrete extended elements 22, and the wall thinning of the precursor web 34 at or near the distal ends 24, the discrete extended elements 22 offer little resistance to the compression or shear imposed on the embossed web 16 by the person's fingers. This lack of resistance is registered as a feeling of softness, much like the feeling of a velour fabric.

Thinning of the precursor web 34 at or near the closed or open distal ends 24 can be measured relative to the thickness of the precursor web 34 or relative to the thickness of the land area that completely surrounds the discrete extended elements 22 of the embossed web 16. The precursor web 34 will typically exhibit thinning of at least about 25%, at least about 50%, or at least about 75% relative to the thickness of the precursor web 34. The precursor web 34 will typically exhibit thinning of at least about 25%, at least about 50%, or at least about 75% relative to the thickness of the land area surrounding the discrete extended elements 22 of the embossed web 16.

It should be noted that a fluid impermeable web having only the discrete extended elements 22 as disclosed herein, and not having macroscopic apertures 12 or discrete extended elements 22 having open distal ends 24, can offer softness for any application in which fluid permeability is not required. Thus, in one embodiment, the process produces an embossed web 16 exhibiting a soft and silky tactile impression on at least one surface thereof, the silky feeling surface of the embossed web 16 exhibiting a pattern of discrete extended elements 22, each of the discrete extended elements 22 being a protruded extension of the web surface and having a side wall defining an open proximal portion and a closed or open distal end 24, the discrete extended elements 22 having a maximum lateral cross-sectional dimension at or near the open proximal portion.

The embossed web 16 can also exhibit improved sound effects. For example, when handled or manually manipulated, the embossed web 16 creates less sound as compared to the precursor web 34. Optionally, certain embossment patterns can create distinctive, desirable sounds when touched or rubbed.

The "area density" of the discrete extended elements 22, which is the number of discrete extended elements 22 per unit area of first surface 26, can be optimized and the embossed web 16 will typically include about 4 to about 10,000, about 95 to about 10,000, about 240 to about 10,000, about 350 to about 10,000, about 500 to about 5,000, or about 700 to about 3,000 discrete extended elements 22 per square centimeter. In general, the center-to-center spacing can be optimized for adequate tactile impression, while at the same time minimizing entrapment of materials, such as fluids, between discrete extended elements 22. The center-to-center spacing between adjacent discrete extended elements 22 can be about 100 microns to about 1,000 microns, about 30 microns to about 800 microns, about 150 microns to about 600 microns, or about 180 microns to about 500 microns.

When the embossed web 16 is utilized as a topsheet for disposable absorbent articles, the embossed web 16 can further include macroapertures that allow fluid to flow through the embossed web 16.

Process for Making Embossed Web

Figure 10:
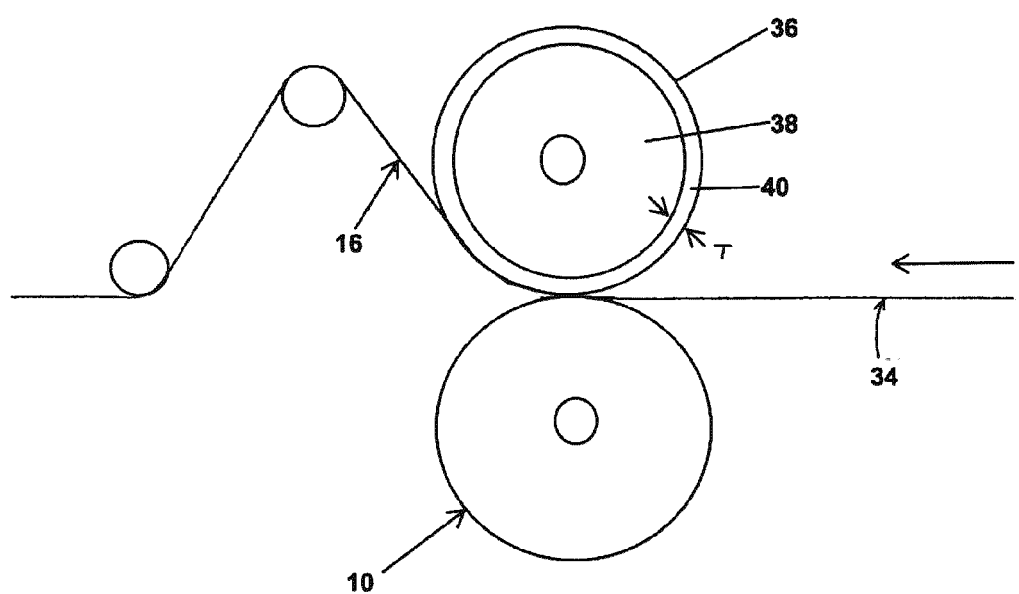
FIG. 10 is a schematic illustration of a continuous process for making an embossed web in accordance with an embodiment of the disclosure.

Referring to FIG. 10, the process for forming an embossed web 16 includes feeding the precursor web 34 between the compliant substrate 36 and the forming structure 10 and applying a pressure between the compliant substrate 36 and the forming structure 10 sufficient to force the compliant substrate 36 into contact with the precursor web 34 and sufficient to force portions of the precursor web 34 into void volumes defined by the apertures 12 or depressions 14 of the forming structure 10 to thereby form an embossed web 16 having discrete extended elements 22. The conformation of the precursor web 34 to the forming structure 10 can be partial conformation, substantial conformation, or complete conformation, depending upon the pressure generated and the topography of the forming structure 10. While not being bound by theory, it is believed that open distal ends 24 can be formed by locally rupturing the precursor web 34 while forcing the precursor web 34 into the apertures 12 or depressions 14 of the forming structure 10.

To obtain permanent deformation of the precursor web 34 to form the embossed web 16, the applied pressure is generally sufficient to stretch the precursor beyond its yield point.

The process can be a batch process or a continuous process. A batch process can involve providing individual sheets of precursor web 34 material placed between the forming structure 10 and compliant substrate 36, each of which is typically in flat-plate form. In one embodiment, the forming structure 10 and compliant substrate 36 are each in the form of flat plates which are placed in a hydraulic press or a clicker press. An example of a hydraulic press is available as Model C from Carver, Inc. The precursor web 34 is placed between the forming structure 10 plate and the compliant substrate 36 plate and pressure is applied by the hydraulic press to conform the precursor web 34 to the forming structure 10 to produce an embossed web 16.

A continuous process can involve providing a roll of precursor web 34 material that is unwound and fed between the forming structure 10 and compliant substrate 36, each of which can be, for example, in the form of a roll. For example, the compliant substrate 36 roll can include a rigid roll, such as a steel roll, that is covered with a compliant material 40. The compliant material 40 can have a thickness of about 3 mm. As the precursor web 34 passes between the forming structure 10 roll and the compliant substrate 36 roll, an embossed web 16 is formed.

The process can have relatively short dwell times. As used herein, the term "dwell time" refers to the amount of time pressure is applied to a given portion of the precursor web 34, usually the amount of time a given portion of the precursor web 34 spends positioned between the forming structure 10 and compliant substrate 36. The pressure is typically applied to the precursor web 34 for a dwell time of less than about 5 seconds, less than about 1 second, less than about 0.1 second, less than about 0.01 second, less than about 0.005 second, or less than about 0.002 second. For example, the dwell time can be about 0.5 milliseconds to about 50 milliseconds.

Even with such relatively short dwell times, embossed webs can be produced with desirable structural features described herein. As a result, the process of the disclosure enables high speed production of embossed webs.

The precursor web 34 can be fed between the forming structure 10 and the compliant substrate 36 at a rate of at least about 0.01 meters per second, at least about 1 meter per second, at least about 5 meters per second, or at least about 10 meters per second. Other suitable rates include, for example, at least about 0.01, 0.05, 0.1, 0.5, 1, 2, 3, 4, 5, 6, 7, 8, 9, or 10 meters per second.

Depending upon factors such as the shape of the apertures 12 or depressions 14 on the forming structure 10 and the pressure applied, the distal ends 24 of the extended elements of the embossed web 16 produced by the process of the disclosure can be either closed or open.

The process can be carried out at ambient temperature, meaning that no heat is intentionally applied to the forming structure 10, compliant substrate 36, and/or precursor web 34. It should be recognized, however, that heat can be generated due to the pressure between the forming structure 10 and the compliant substrate 36, especially in a continuous process. As a result, the forming structure 10 and/or the compliant substrate 36 may be cooled in order to maintain the process conditions at the desired temperature, such as ambient temperature and to improve the durability of the compliant substrate.

The process can also be carried out with the precursor web 34 having an elevated temperature. For example, the temperature of the precursor web 34 can be less than the melting point of the precursor web 34. For example, the temperature of the precursor web 34 can be at least about 10° C. below the melting point of the precursor web 34. The precursor web 34, especially a precursor web 34 including polyethylenes, can have a temperature during the process of about 10° C. to about 120° C., about 20° C. to about 110° C., about 10° C. to about 80° C., or about 10° C. to about 40° C. The precursor web 34 can be heated during the process by heating the precursor web 34, the compliant substrate 36, and/or the forming structure 10.

In one embodiment, the precursor web is not heated before being provided between the forming structure and the compliant substrate. In another embodiment, the precursor web, the forming structure and the compliant substrate are not heated before providing the precursor web between the forming structure and the compliant substrate.

In general, the process of the present invention can be carried out at a temperature of from about 10° C. to about 200° C., from about 10° C. to about 120° C., from about 10° C. to about 80° C., or from about 10° C. to about 40° C. The temperature can be measured by, for example, a non-contact thermometer, such as an infrared thermometer or a laser thermometer, measuring the temperature at the nip between the compliant substrate 36 and forming structure 10. The temperature can also be determined using temperature sensitive material such as Thermolabel available from Paper Thermometer Company.

An average pressure is provided between the compliant substrate 36 and the forming structure 10. The average pressure is sufficient to force the precursor web 34, which is positioned between the forming structure 10 and compliant substrate 36, into the discrete apertures 12 or depressions 14 of the forming structure 10 to form an embossed web 16. In general, the average pressure provided between the forming structure 10 and compliant substrate 36 is about 1 MPa to about 100 MPa, about 5 MPa to about 70 MPa, about 10 MPa to about 60 MPa, or about 20 MPa to about 40 MPa. For example, the applied pressure can be up to about 30 MPa.

The average pressure provided between the forming structure 10 and the compliant substrate 36 can be determined as a force per unit area. A force is applied to the forming structure 10 and/or compliant substrate 36 so that the compliant substrate 36 becomes impressed against the forming structure 10 to a desired compression distance, as described hereinbelow. The unit area is the area of the "contact patch" between the forming structure 10 and the compliant substrate 36. From these values, an average pressure between the forming structure 10 and compliant substrate 36 can be calculated.

If the forming structure 10 and compliant substrate 36 are both flat plates, the area of the contact patch between the forming structure 10 and compliant substrate 36 is typically easily determined based on the dimensions of the flat plates.

If the forming structure 10 and the compliant substrate 36 are both rolls, the area of the contact patch between the forming structure 10 and compliant substrate 36 can be determined by static loading of the rolls with a piece of pressure sensitive film provided between the rolls. A suitable pressure sensitive film is Fuji Prescale Film available from FUJIFILM NDT Systems, which undergoes certain color changes upon application of pressure to the film. The static loading on the rolls is released and the pressure sensitive film is removed from the rolls. The pressure sensitive film will have a color-changed area that represents the contact patch between the forming structure 10 and compliant substrate 36. Using this contact patch area and the force applied to the forming structure 10 roll and/or compliant structure 10 roll, the average pressure provided between the forming structure 10 roll and compliant structure 10 roll can be calculated.

The forming structure 10 and compliant substrate 36 are impressed to a desired compression distance by applying a force to the forming structure 10 and/or compliant substrate 36. The "compression distance" is determined by measuring the distance the forming structure 10 is pressed against the compliant substrate 36. This distance can be measured by bringing the forming structure 10 and compliant substrate 36 into initial contact and then forcing the forming structure 10 and compliant substrate 36 together. The distance that the forming structure 10 and compliant substrate 36 are moved relative to each other subsequent to the initial contact is referred to as the "compression distance". If the forming structure 10 and compliant substrate 36 are both rolls, the compression distance can be measured as the change in distance between the rotational axis of the forming structure 10 and the rotational axis of the compliant substrate 36 due to the force applied after initial contact.

The compression distance of the forming structure 10 to the compliant substrate 36 will typically be about 1 mm to 10 mm, about 0.1 mm to about 5 mm, about 0.2 mm to about 4 mm, or about 0.3 mm to about 3 mm.

The forming structure 10 and compliant substrate 36 can be utilized in a low strain rate process, such as that described in U.S. Application No. 2008/0224351 A1, to produce an embossed web 16. Such a process is encompassed by the disclosure.

The process can optionally further include applying a slip agent to the precursor web 34, forming structure 10, and/or compliant substrate 36 before the precursor web 34 is provided between the forming structure 10 and the compliant substrate 36. The can be beneficial, especially in a continuous process, to reduce friction between the precursor web 34 and the forming structure 10. Non-limiting examples of suitable slip agents include silicone, talc, lubricating oils, and the like.

The process can optionally include applying a positive pressure to the embossed web to reinvert discrete extended elements 22 that may have inverted during removal of the embossed web from between the forming structure 10 and the compliant substrate 36. The inverted discrete extended elements 22 can be reinverted to extend from the embossed web first surface 26 by applying a positive pressure, such as from an air knife, sufficient to reinvert the inverted discrete extended elements 22.

The process can optionally be combined with other processes to further manipulate the embossed web 16. In one embodiment, such additional processes can be combined with the process on the same process manufacturing line to produce, for example, absorbent articles. In one embodiment, the process is combined with a process that can impart macroapertures in the embossed web 16, such as the process described in US 2006/0087053 A1 or US 2005/0064136 A1. Such a process combination can produce a macroapertured embossed web 16 that can be suitable for use as a topsheet in an absorbent article. Such a macroapertured embossed web 16 can be subsequently converted into an absorbent article by combining it with other absorbent article components, such as absorbent cores, backsheets, and the like, preferably on the same process manufacturing line.

In addition to the processes described hereinbefore, alternative processes for making embossed webs are contemplated. The process can further include applying pressure from a second pressure source, e.g. a pressure source in addition to the first compliant substrate. The second pressure source can be selected from the group consisting of a static liquid pressure plenum, a static gas pressure plenum, a velocity gas pressure source, such as an air knife, a velocity liquid pressure source, such as is used in conventional hydroforming process, and a compliant substrate. Co-pending U.S. patent application Ser. No. 12/721,989, filed Mar. 11, 2010 entitled "PROCESS FOR MAKING AN EMBOSSED WEB", discloses a suitable static pressure plenum for use in the process of the present disclosure. Other suitable static pressure plenums for use in the process of the present disclosure include those described in U.S. Provisional patent application Ser. No. 13/045,991, filed Mar. 11, 2010 entitled "APPARATUS FOR EMBOSSING A WEB", and in U.S. Pat. No. 5,972,280. The pressures exerted on the precursor web 34 by the second pressure source will typically be similar to those pressures exerted on the precursor web 34 by the compliant substrate described hereinbefore. The second pressure source can apply a pressure against the precursor web before or after the compliant substrate. In one embodiment, at least two compliant substrates are provided and pressure is applied on a first portion of the precursor web 34 between the forming structure 10 and the first compliant substrate. Pressure can then be applied on the first portion of the precursor web 34 between the forming structure 10 and the second compliant substrate. This can further force the portion of the precursor web registered to the same apertures or depressions of the forming structure. This can allow for enhancement of the discrete extended elements 22 formed by the process.

Uses of Embossed Web

The embossed webs can be utilized in a number of different ways, including as component materials of absorbent articles (such as topsheets, backsheets or release paper wrappers), packaging (such as flow wrap, shrink wrap, or polybags), trash bags, food wrap, dental floss, wipes, electronic components, wall paper, clothing, aprons, window coverings, placemats, book covers, and the like.

EXAMPLES

Example 1

Embossed webs were produced using a compliant substrate 36 of 5.88 mm thick 40 A Gum Rubber and a forming structure 10 having about 486 apertures per square centimeter. The compliant substrate 36 had a Shore A hardness of about 40. The compliant substrate was in the form of a sheet 25.4 mm×25.4 mm square.

The forming structure had a thickness of about 2.25 mm. The apertures had a circular cross-section with an about 250 micron diameter at the top surface and a 2° taper from a top surface of the aperture into the depth of the aperture. The apertures had an edge-to-edge spacing of about 200 microns.

The precursor web 34 utilized was a polyethylene/polypropylene blend film obtained from RKW US, Inc. that was about 15 microns thick and had a basis weight of 14.2 grams per square meter ("gsm").

The embossing process was performed using a high speed research press at room temperature. The high speed research press is described in detail in U.S. Patent Publication No. 2009/0120308, and is designed to simulate a continuous production line process for embossing the precursor web 34. The press was operated to simulate compliant substrate and forming structure roll diameters of 205 mm. The precursor web 34 was fed between the forming structure 10 and the compliant substrate 36 at a simulated rate of about 2.74 m/sec and about 7 m/sec.

Figure 11:
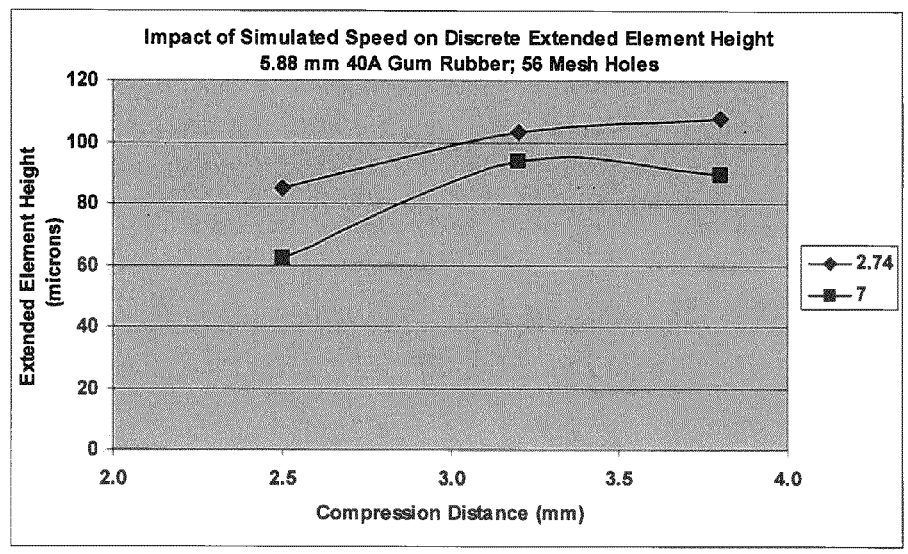
FIG. 11 is a graph illustrating the average height of the discrete extended elements as a function of compression distance and feed rate.

The compression distance between the compliant substrate and the forming structure, the applied pressure, and the compressive strain in the compliant substrate along with the average height of the discrete extended elements 22 of the embossed webs are shown in Table 1. FIG. 11 illustrates the effect of feed rate and compression distance on discrete extended element height.

TABLE 1

|  | | Average Discrete Extended Element Height (microns) | | Applied Pressure (MPa) | | Dwell Time (milliseconds) | | Compressive Strain | |
| --- | --- | --- | --- | --- | --- | --- | --- | --- | --- |
|  | | 2.74 m/s Feed Rate | 7 m/s Feed Rate | 2.74 m/s Feed Rate | 7 m/s Feed Rate | 2.74 m/s Feed Rate | 7 m/s Feed Rate | 2.74 m/s Feed Rate | 7 m/s Feed Rate |
| Compression Distance (mm) | 2.5 | 85 | 62 | 6.3 | 6.3 | 12.4 | 4.9 | 0.43 | 0.43 |
|  | 3.2 | 103 | 94 | 8.9 | 8.9 | 13.4 | 5.3 | 0.54 | 0.54 |
|  | 3.8 | 108 | 90 | 12.9 | 14.3 | 14.4 | 5.7 | 0.65 | 0.65 |

The data illustrates that the extended element height generally increases with increasing compression distance and as the feed rate increases the average height of the discrete extended elements decreases.

Example 2

Embossed webs were produced using a compliant substrate 36 of 3.28 mm thick 40A Gum Rubber and a forming structure 10 having about 1550 apertures per square centimeter. The compliant substrate 36 had a Shore A hardness of about 40. The compliant substrate was in the form of a sheet 25.4 mm×25.4 mm square.

The forming structure had a thickness of about 1.02 mm. The apertures had a circular cross-section with an about 147 micron diameter at the top surface and a 2° taper from a top surface of the aperture into the depth of the aperture. The apertures had an edge-to-edge spacing of about 107 microns.

The precursor web 34 utilized was a polyethylene/polypropylene blend film obtained from RKW US, Inc. that was about 15 microns thick and had a basis weight of 14.2 grams per square meter ("gsm").

The embossing process was performed using a high speed research press, as described in the preceding example. The press was operated to simulate compliant substrate and forming structure roll diameters of 205 mm. The precursor web 34 was fed between the forming structure 10 and the compliant substrate 36 at a simulated rate of 6 m/sec.

The compression distance between the compliant substrate and the forming structure, the applied pressure, and strain rates along with the average height of the discrete extended elements 22 of the embossed webs is shown in Table 2.

|  | Compressive Distance (mm) | Average Discrete Extended Element Height (microns) | Dwell Time (Milliseconds) | Applied Pressure (MPa) | Compressive Strain |
| --- | --- | --- | --- | --- | --- |
| Sample 1 | 1.2 | 48 | 3.7 | 11.7 | 0.37 |
| Sample 2 | 1.3 | 62 | 3.9 | 14.9 | 0.40 |

Figure 12:
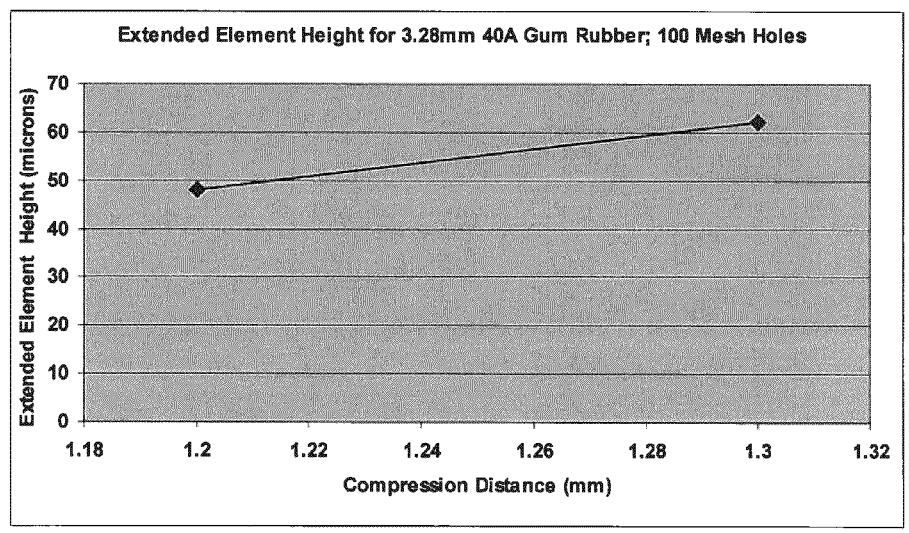
FIG. 12 is a graph illustrating the average height of the discrete extended elements as a function of compression distance.

The data illustrates that as the compression distance increases, the required pressure and the average height of the discrete extended elements increases (FIG. 12).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

When a technical feature is disclosed herein in relation to one embodiment, this feature can be combined with any other feature(s) disclosed in other embodiment(s) or claim(s), unless stated otherwise.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for forming an embossed web, the process comprising:

feeding a precursor web between a compliant substrate and a forming structure comprising land areas and a plurality of discrete apertures, discrete depressions, or combinations thereof, the apertures or depressions having a depth of at least substantially equal to a thickness of the precursor web, adjacent apertures or depressions being separated by land areas and having an edge-to-edge spacing greater than about 30 microns, wherein the forming structure includes at least about 95 discrete apertures or discrete depressions per square centimeter; and, applying pressure between the compliant substrate and the forming structure sufficient to force the compliant substrate into contact with the precursor web and sufficient to force portions of the precursor web into void volumes defined by the apertures or depressions, thereby forming the embossed web comprising a plurality of discrete extended elements having open proximal ends, individual discrete extended elements being completely surrounded by land areas, wherein the discrete extended elements each have a height of at least about 50 microns and an aspect ratio of at least about 0.3.

2. The process of claim 1, further comprising feeding the precursor web between the compliant substrate and the forming structure at a rate of at least about 1 meter per second.

3. The process of claim 1, further comprising applying pressure between the compliant substrate and the forming structure for a dwell time of about 0.5 millisecond to about 5 seconds.

4. The process of claim 1, wherein the temperature of the precursor web during the process is less than the melting point of the precursor web.

5. The process of claim 4, wherein the temperature of the precursor web during the process is at least about 10° C. below the melting point of the precursor web.

6. The process of claim 1, wherein the compliant substrate comprises a material selected from the group consisting of elastomers, felts, liquid filled bladders, gas filled bladders, and combinations thereof.

7. The process of claim 6, wherein the compliant substrate is a porous elastomer.

8. The process of claim 1, wherein the compliant substrate has compression recovery such that the compliant substrate rebounds fast enough to facilitate the process, wherein the process is a continuous process.

9. The process of claim 1, wherein the compliant substrate has a Shore A hardness of about 30 durometers to about 80 durometers.

10. The process of claim 1, wherein the apertures or depressions of the forming structure have an average edge-to-edge spacing of about 30 microns to about 640 microns.

11. The process of claim 1, wherein the apertures of the forming structure having an average width of about 10 microns to about 5 mm.

12. The process of claim 1, wherein the forming structure comprises a plurality of discrete depressions, and the depressions have a depth of about 90 microns to about 5000 microns.

13. The process of claim 1, wherein the discrete extended elements have an open distal end.

14. The process of claim 1, wherein the discrete extended elements have a closed, distal end.

15. The process of claim 1, Wherein the discrete extended elements have an aspect ratio of at least about 0.5.

16. The process of claim 1, wherein the applied pressure is about 1 MPa to about 100 MPa.

17. The process of claim 1 wherein the discrete extended elements are thinned relative to the thickness of the precursor web.

18. The process of claim 1, wherein the applied pressure is sufficient to stretch the precursor web beyond its yield point.

19. The process of claim 1, wherein the precursor web is selected, from the group consisting of polyethylene, polypropylene, and combinations thereof.

20. The process of claim 1, further comprising applying a pressure from a second pressure source against the precursor web opposite the forming structure sufficient to force portions of the precursor web into void volumes defined by the apertures or depressions.

21. The process of claim 20, wherein the second pressure source is selected from the group consisting of a static liquid pressure plenum, a static gas pressure plenum, a velocity gas pressure source, a velocity liquid pressure source, and a compliant substrate.

* * * * *